US012575892B2

(12) United States Patent
Sowards et al.

(10) Patent No.: US 12,575,892 B2
(45) Date of Patent: Mar. 17, 2026

(54) ULTRASOUND DETECTION SYSTEM

(71) Applicant: Bard Access Systems, Inc., Salt Lake City, UT (US)

(72) Inventors: Steffan Sowards, Salt Lake City, UT (US); William Robert McLaughlin, Bountiful, UT (US); Anthony K. Misener, Bountiful, UT (US); Shayne Messerly, Kaysville, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 703 days.

(21) Appl. No.: 17/845,818

(22) Filed: Jun. 21, 2022

(65) Prior Publication Data

US 2022/0401157 A1 Dec. 22, 2022

Related U.S. Application Data

(60) Provisional application No. 63/213,576, filed on Jun. 22, 2021.

(51) Int. Cl.
*A61B 8/08* (2006.01)
*A61B 8/00* (2006.01)
(Continued)

(52) U.S. Cl.
CPC ............ *A61B 34/20* (2016.02); *A61B 8/0841* (2013.01); *A61B 8/085* (2013.01); *A61B 8/465* (2013.01); *A61B 17/3403* (2013.01); *A61B 90/13* (2016.02); *A61B 2017/3413* (2013.01); *A61B 2034/107* (2016.02); *A61B 2034/2051* (2016.02)

(58) Field of Classification Search
CPC ........................ A61B 90/13; A61B 2017/3413
See application file for complete search history.

(56) References Cited

U.S. PATENT DOCUMENTS

| | | | |
|---|---|---|---|
| 5,325,293 A | 6/1994 | Dorne | |
| 5,549,554 A | 8/1996 | Miraki | |
| (Continued) | | | |

FOREIGN PATENT DOCUMENTS

| | | | |
|---|---|---|---|
| CN | 101854853 A | 10/2010 | |
| CN | 105054962 A | 11/2015 | |
| (Continued) | | | |

OTHER PUBLICATIONS

PCT/US2022/034380 filed Jun. 21, 2022 International Search Report and Written Opinion dated Oct. 5, 2022.
(Continued)

*Primary Examiner* — Colin T. Sakamoto
(74) *Attorney, Agent, or Firm* — Rutan & Tucker LLP

(57) ABSTRACT

Disclosed herein is an ultrasound imaging system configured to guide medical device insertion. The ultrasound imaging system includes an ultrasound probe having an ultrasound generation device configured to detect one or more anatomical targets within a target area, and one or more projectors configured to project one or more icons within the target area. The ultrasound imaging system can also include a console configured to generate the one or more icons. The console can be coupled to the ultrasound probe, and be in communication with each of the ultrasound generation device and the one or more projectors.

20 Claims, 5 Drawing Sheets

(51) Int. Cl.

| | |
|---|---|
| *A61B 17/34* | (2006.01) |
| *A61B 34/20* | (2016.01) |
| *A61B 90/13* | (2016.01) |
| *A61B 34/10* | (2016.01) |

(56) References Cited

U.S. PATENT DOCUMENTS

| | | | |
|---|---|---|---|
| 5,573,529 A | 11/1996 | Haak et al. | |
| 5,908,387 A | 6/1999 | LeFree et al. | |
| 5,970,119 A | 10/1999 | Hofmann | |
| 5,997,497 A | 12/1999 | Nita et al. | |
| 6,012,034 A | 1/2000 | Hamparian et al. | |
| 6,074,367 A | 6/2000 | Hubbell | |
| 6,543,642 B1 | 4/2003 | Milliorn | |
| 6,554,771 B1 | 4/2003 | Buil et al. | |
| 6,592,565 B2 | 7/2003 | Twardowski | |
| 6,601,705 B2 | 8/2003 | Molina et al. | |
| 6,612,992 B1 | 9/2003 | Hossack et al. | |
| 6,613,002 B1 | 9/2003 | Clark et al. | |
| 6,687,386 B1 | 2/2004 | Ito et al. | |
| 6,702,749 B2 | 3/2004 | Paladini et al. | |
| 6,754,608 B2 | 6/2004 | Svanerudh et al. | |
| 6,840,379 B2 | 1/2005 | Franks-Farah et al. | |
| 6,857,196 B2 | 2/2005 | Dalrymple | |
| 7,831,449 B2 | 11/2010 | Ying et al. | |
| 9,521,961 B2 | 12/2016 | Silverstein et al. | |
| 9,756,766 B2 | 9/2017 | Best | |
| 9,949,720 B2 | 4/2018 | Southard et al. | |
| 9,950,139 B2 | 4/2018 | Blanchard et al. | |
| 10,849,689 B1 | 12/2020 | Hu et al. | |
| 11,462,324 B1 | 10/2022 | Roh et al. | |
| 11,844,656 B2 | 12/2023 | Urabe et al. | |
| 11,896,425 B2 | 2/2024 | Dhatt et al. | |
| 11,974,813 B1 | 5/2024 | Donhowe et al. | |
| 2003/0028112 A1* | 2/2003 | Paladini | A61B 8/0833 600/439 |
| 2003/0047126 A1 | 3/2003 | Tomaschko | |
| 2003/0106825 A1 | 6/2003 | Molina et al. | |
| 2003/0120154 A1* | 6/2003 | Sauer | A61B 8/0841 600/459 |
| 2003/0120155 A1* | 6/2003 | Sauer | A61B 8/00 600/464 |
| 2003/0199765 A1* | 10/2003 | Stetten | A61B 8/00 600/439 |
| 2004/0055925 A1 | 3/2004 | Franks-Farah et al. | |
| 2005/0000975 A1 | 1/2005 | Carco et al. | |
| 2005/0165299 A1 | 7/2005 | Kressy et al. | |
| 2006/0004290 A1 | 1/2006 | Smith et al. | |
| 2006/0015039 A1 | 1/2006 | Cassidy et al. | |
| 2006/0020256 A1 | 1/2006 | Bell et al. | |
| 2007/0043341 A1 | 2/2007 | Anderson et al. | |
| 2007/0073155 A1 | 3/2007 | Park et al. | |
| 2007/0199848 A1 | 8/2007 | Ellswood et al. | |
| 2007/0239120 A1 | 10/2007 | Brock et al. | |
| 2007/0249911 A1 | 10/2007 | Simon | |
| 2007/0260213 A1 | 11/2007 | Williams et al. | |
| 2008/0009747 A1 | 1/2008 | Saadat et al. | |
| 2008/0033293 A1 | 2/2008 | Beasley et al. | |
| 2008/0033759 A1 | 2/2008 | Finlay | |
| 2008/0051657 A1 | 2/2008 | Rold | |
| 2008/0058963 A1 | 3/2008 | Garibaldi et al. | |
| 2008/0161687 A1 | 7/2008 | Suri et al. | |
| 2008/0177186 A1 | 7/2008 | Slater et al. | |
| 2008/0218743 A1* | 9/2008 | Stetten | A61B 90/36 356/73 |
| 2008/0300491 A1 | 12/2008 | Bonde et al. | |
| 2009/0143672 A1 | 6/2009 | Harms et al. | |
| 2009/0143684 A1 | 6/2009 | Cermak et al. | |
| 2009/0156926 A1 | 6/2009 | Messerly et al. | |
| 2009/0182224 A1 | 7/2009 | Shmarak et al. | |
| 2009/0221908 A1* | 9/2009 | Glossop | A61B 5/066 382/128 |
| 2009/0234328 A1 | 9/2009 | Cox et al. | |
| 2009/0306509 A1 | 12/2009 | Pedersen et al. | |
| 2010/0080427 A1 | 4/2010 | Yeluri et al. | |
| 2010/0106015 A1* | 4/2010 | Norris | A61B 17/3403 600/437 |
| 2010/0106056 A1* | 4/2010 | Norris | A61B 8/42 600/437 |
| 2010/0211026 A2 | 8/2010 | Sheetz et al. | |
| 2010/0305442 A1 | 12/2010 | Tierney et al. | |
| 2010/0312121 A1 | 12/2010 | Guan | |
| 2011/0028847 A1 | 2/2011 | Whitmore, III et al. | |
| 2011/0071404 A1 | 3/2011 | Schmitt et al. | |
| 2011/0166451 A1 | 7/2011 | Blaivas et al. | |
| 2011/0245659 A1* | 10/2011 | Ma | A61B 8/0841 600/424 |
| 2011/0295108 A1 | 12/2011 | Cox et al. | |
| 2011/0313293 A1 | 12/2011 | Lindekugel et al. | |
| 2012/0078103 A1 | 3/2012 | Tashiro et al. | |
| 2012/0143029 A1 | 6/2012 | Silverstein et al. | |
| 2012/0165679 A1 | 6/2012 | Orome et al. | |
| 2012/0197132 A1 | 8/2012 | O'Connor | |
| 2012/0253200 A1 | 10/2012 | Stolka et al. | |
| 2013/0006102 A1* | 1/2013 | Wilkes | A61B 5/283 600/424 |
| 2013/0102889 A1 | 4/2013 | Southard et al. | |
| 2013/0131499 A1 | 5/2013 | Chan et al. | |
| 2013/0218024 A1 | 8/2013 | Boctor et al. | |
| 2013/0261553 A1 | 10/2013 | Sheldon et al. | |
| 2014/0155744 A1 | 6/2014 | Pameijer | |
| 2014/0275997 A1 | 9/2014 | Chopra et al. | |
| 2014/0287393 A1 | 9/2014 | Kumar et al. | |
| 2014/0303423 A1 | 10/2014 | Amthor et al. | |
| 2014/0343406 A1 | 11/2014 | Damjanovic | |
| 2015/0148668 A1 | 5/2015 | Stolka et al. | |
| 2015/0182144 A1 | 7/2015 | Bharat et al. | |
| 2015/0216442 A1 | 8/2015 | Lavy et al. | |
| 2015/0250437 A1 | 9/2015 | Zaiki | |
| 2015/0272553 A1 | 10/2015 | Thattari Kandiyil et al. | |
| 2015/0320325 A1 | 11/2015 | Sheehan et al. | |
| 2015/0320481 A1 | 11/2015 | Cosman, Jr. et al. | |
| 2015/0359991 A1 | 12/2015 | Dunbar et al. | |
| 2016/0051224 A1* | 2/2016 | Striano | A61B 8/4455 600/461 |
| 2016/0128719 A1 | 5/2016 | Cermak | |
| 2016/0174937 A1 | 6/2016 | Bakshi et al. | |
| 2016/0213398 A1 | 7/2016 | Liu | |
| 2016/0300120 A1 | 10/2016 | Haas et al. | |
| 2016/0302772 A1 | 10/2016 | Cummins et al. | |
| 2016/0331469 A1 | 11/2016 | Hall et al. | |
| 2016/0374644 A1 | 12/2016 | Mauldin, Jr. et al. | |
| 2017/0035514 A1 | 2/2017 | Fox et al. | |
| 2017/0056062 A1* | 3/2017 | Buljubasic | A61B 5/150748 |
| 2017/0079551 A1 | 3/2017 | Henkel et al. | |
| 2017/0188990 A1 | 7/2017 | Von Allmen et al. | |
| 2017/0245831 A1 | 8/2017 | Nishigaki et al. | |
| 2017/0265946 A1 | 9/2017 | Ramachandran et al. | |
| 2017/0290563 A1 | 10/2017 | Cole et al. | |
| 2018/0015256 A1 | 1/2018 | Southard et al. | |
| 2018/0036084 A1 | 2/2018 | Krimsky | |
| 2018/0061546 A1 | 3/2018 | Ma et al. | |
| 2018/0125450 A1 | 5/2018 | Blackbourne et al. | |
| 2018/0132944 A1 | 5/2018 | Yan et al. | |
| 2018/0228465 A1 | 8/2018 | Southard et al. | |
| 2018/0289929 A1 | 10/2018 | Ma et al. | |
| 2018/0310955 A1 | 11/2018 | Lindekugel et al. | |
| 2019/0000478 A1 | 1/2019 | Messerly et al. | |
| 2019/0026438 A1 | 1/2019 | Ma et al. | |
| 2019/0105017 A1* | 4/2019 | Hastings | A61B 8/4444 |
| 2019/0282262 A1* | 9/2019 | Bouazza-Marouf | A61B 17/3403 |
| 2019/0298278 A1 | 10/2019 | Nachabe et al. | |
| 2019/0374290 A1 | 12/2019 | Stolka et al. | |
| 2020/0090331 A1 | 3/2020 | Mansi et al. | |
| 2020/0113540 A1 | 4/2020 | Gijsbers et al. | |
| 2020/0219258 A1 | 7/2020 | Saget et al. | |
| 2020/0230391 A1 | 7/2020 | Burkholz et al. | |
| 2020/0234812 A1 | 7/2020 | Willybiro et al. | |
| 2020/0237403 A1 | 7/2020 | Southard et al. | |
| 2020/0245969 A1 | 8/2020 | Tung et al. | |
| 2020/0275949 A1* | 9/2020 | Masotti | A61B 8/461 |
| 2020/0297235 A1 | 9/2020 | Sanchez et al. | |
| 2020/0315592 A1 | 10/2020 | Soleimani et al. | |

(56) References Cited

U.S. PATENT DOCUMENTS

| | | |
|---|---|---|
| 2020/0359990 A1 | 11/2020 | Poland et al. |
| 2021/0015448 A1 | 1/2021 | Sokulin et al. |
| 2021/0045717 A1 | 2/2021 | Schwab |
| 2021/0059636 A1 | 3/2021 | Durfee et al. |
| 2021/0085282 A1 | 3/2021 | Prince |
| 2021/0138130 A1 | 5/2021 | Kotanko et al. |
| 2021/0169585 A1 | 6/2021 | Prince et al. |
| 2021/0186456 A1 | 6/2021 | Prince |
| 2021/0201080 A1 | 7/2021 | Kitahara |
| 2021/0275256 A1 | 9/2021 | Sowards et al. |
| 2021/0315542 A1 | 10/2021 | Oura et al. |
| 2021/0322106 A1 | 10/2021 | Mo et al. |
| 2022/0013218 A1 | 1/2022 | Cousin |
| 2022/0022969 A1 | 1/2022 | Misener |
| 2022/0027257 A1 | 1/2022 | Harutyunyan et al. |
| 2022/0039685 A1 | 2/2022 | Misener et al. |
| 2022/0054869 A1 | 2/2022 | Stein et al. |
| 2022/0096797 A1 | 3/2022 | Prince |
| 2022/0101980 A1 | 3/2022 | Rothenberg et al. |
| 2022/0104886 A1 | 4/2022 | Blanchard et al. |
| 2022/0117582 A1 | 4/2022 | McLaughlin et al. |
| 2022/0142608 A1 | 5/2022 | Matsumoto |
| 2022/0160434 A1 | 5/2022 | Messerly et al. |
| 2022/0189610 A1 | 6/2022 | Long et al. |
| 2022/0230714 A1 | 7/2022 | Batman et al. |
| 2022/0241014 A1 | 8/2022 | Kleyman et al. |
| 2022/0280246 A1 | 9/2022 | Messerly et al. |
| 2022/0304652 A1 | 9/2022 | Peterson et al. |
| 2022/0392642 A1 | 12/2022 | Dasi et al. |
| 2022/0406460 A1 | 12/2022 | Golan et al. |
| 2023/0030941 A1 | 2/2023 | Han |
| 2023/0121370 A1 | 4/2023 | Sowards et al. |
| 2023/0147164 A1 | 5/2023 | Sowards et al. |
| 2023/0148993 A1 | 5/2023 | Sowards et al. |
| 2023/0225702 A1 | 7/2023 | Sakalauskas |
| 2023/0260107 A1 | 8/2023 | Dhatt et al. |
| 2023/0329748 A1 | 10/2023 | Sowards et al. |
| 2023/0338003 A1 | 10/2023 | Misener et al. |
| 2023/0380906 A1 | 11/2023 | Misener et al. |
| 2023/0404683 A1 | 12/2023 | Schmidt et al. |
| 2023/0420105 A1 | 12/2023 | Misener et al. |
| 2024/0008894 A1 | 1/2024 | Sowards et al. |
| 2024/0245386 A1 | 7/2024 | Prince |
| 2024/0274297 A1 | 8/2024 | Sillesen et al. |
| 2024/0390605 A1 | 11/2024 | Burkholz et al. |
| 2025/0000585 A1 | 1/2025 | Sinha et al. |
| 2025/0255576 A1 | 8/2025 | Prince |

FOREIGN PATENT DOCUMENTS

| | | |
|---|---|---|
| CN | 216167530 U | 4/2022 |
| EP | 1504713 A1 | 2/2005 |
| EP | 0788329 B1 | 12/2006 |
| JP | 2018175547 A | 11/2018 |
| KR | 20180070878 A | 6/2018 |
| WO | 2013059714 A1 | 4/2013 |
| WO | 2014053934 A1 | 4/2014 |
| WO | 2015/017270 A1 | 2/2015 |
| WO | 2018/026878 A1 | 2/2018 |
| WO | 2019/232451 A1 | 12/2019 |
| WO | 2020/002620 A1 | 1/2020 |
| WO | 2020150501 A1 | 7/2020 |
| WO | 2020160550 A1 | 8/2020 |
| WO | 2020/186198 A1 | 9/2020 |
| WO | 2021113733 A1 | 6/2021 |
| WO | 2022/067101 A1 | 3/2022 |
| WO | 2022/072727 A2 | 4/2022 |
| WO | 2022/081904 A1 | 4/2022 |
| WO | 2022150411 A1 | 7/2022 |
| WO | 2022/187701 A1 | 9/2022 |
| WO | 2022212414 A1 | 10/2022 |
| WO | 2022/271728 A1 | 12/2022 |
| WO | 2023064492 A1 | 4/2023 |
| WO | 2023081414 A1 | 5/2023 |
| WO | 2023091427 A1 | 5/2023 |
| WO | 2023205019 A1 | 10/2023 |
| WO | 2023205052 A1 | 10/2023 |
| WO | 2023230284 A1 | 11/2023 |
| WO | 2023244640 A1 | 12/2023 |
| WO | 2023250001 A1 | 12/2023 |
| WO | 2024010874 A1 | 1/2024 |

OTHER PUBLICATIONS

U.S. Appl. No. 17/112,735, filed Dec. 4, 2022 Non-Final Office Action dated Oct. 26, 2022.

PCT/US2022/046606 filed Oct. 13, 2022 International Search Report and Written Opinion dated Feb. 6, 2023.

PCT/US2022/049042 filed Nov. 4, 2022 International Search Report and Written Opinion dated Mar. 1, 2023.

PCT/US2022/049989 filed Nov. 15, 2022 International Search Report and Written Opinion dated Feb. 6, 2023.

U.S. Appl. No. 17/112,725, filed Dec. 4, 2020 Final Office Action dated Apr. 14, 2023.

U.S. Appl. No. 17/485,035, filed Sep. 24, 2021 Non-Final Office Action dated May 3, 2023.

U.S. Appl. No. 17/725,370, filed Apr. 20, 2022 Restriction Requirement dated Apr. 27, 2023.

Murphy, Ethan K., et al., "Phantom Studies of Fused-Data TREIT Using Only Biopsy-Probe Electrodes" IEEE Transactions on Medical Imaging, IEEE, USA. vol. 39 No. 114, May 2020. (May 4, 2020).

PCT/US2012/061182 International Seach Report and Written Opinion dated Mar. 11, 2013.

PCT/US2020/063441 filed Dec. 4, 2020 International Preliminary Report on Patentability dated May 17, 2022.

PCT/US2020/063441 filed Dec. 4, 2020 International Search Report and Written Opinion dated Mar. 19, 2021.

PCT/US2021/052055 filed Sep. 24, 2021 International Search Report and Written Opinion dated Dec. 20, 2021.

PCT/US2022/019017 filed Mar. 4, 2022 International Search Report and Written Opinion dated Jun. 14, 2022.

PCT/US2022/022400 filed Mar. 29, 2022 International Search Report and Written Opinion dated Jul. 8, 2022.

Sebastian Vogt: "Real-Time Augmented Reality for Image-Guided Interventions", Oct. 5, 2009, XPO55354720, Retrieved from the Internet: URL: https://opus4.kobv.de/opus4-fau/frontdoor/deliver/index/docId/1235/file/SebastianVogtDissertation.pdf.

U.S. Appl. No. 13/656,563, filed Oct. 19, 2012 Decision on Appeal dated Nov. 1, 2017.

U.S. Appl. No. 13/656,563, filed Oct. 19, 2012 Examiner's Answer dated Nov. 16, 2015.

U.S. Appl. No. 13/656,563, filed Oct. 19, 2012 Final Office Action dated Dec. 5, 2014.

U.S. Appl. No. 13/656,563, filed Oct. 19, 2012 Non-Final Office Action dated Jul. 18, 2014.

U.S. Appl. No. 15/951,903, filed Apr. 12, 2018 Advisory Action dated Dec. 22, 2020.

U.S. Appl. No. 15/951,903, filed Apr. 12, 2018 Board Decision dated Apr. 20, 2022.

U.S. Appl. No. 15/951,903, filed Apr. 12, 2018 Examiner's Answer dated Jun. 3, 2021.

U.S. Appl. No. 15/951,903, filed Apr. 12, 2018 Final Office Action dated Oct. 13, 2020.

U.S. Appl. No. 15/951,903, filed Apr. 12, 2018 Non-Final Office Action dated May 22, 2020.

U.S. Appl. No. 15/951,903, filed Apr. 12, 2018 Notice of Allowance dated May 2, 2022.

William F Garrett et al: "Real-time incremental visualization of dynamic ultrasound volumes using parallel BSP trees", Visualization '96. Proceedings, IEEE, NE, Oct. 27, 1996, pp. 235-ff, XPO58399771, ISBN: 978-0-89791-864-0 abstract, figures 1-7, pp. 236-240.

U.S. Appl. No. 17/687,476, filed Mar. 4, 2022 Non-Final Office Action dated Nov. 1, 2024.

U.S. Appl. No. 17/707,662, filed Mar. 29, 2022 Examiner's Answer dated Oct. 23, 2024.

(56)                References Cited

OTHER PUBLICATIONS

U.S. Appl. No. 17/724,371, filed Apr. 19, 2022 Advisory Action dated Sep. 20, 2024.
U.S. Appl. No. 17/724,371, filed Apr. 19, 2022 Non-Final Office Action dated Nov. 26, 2024.
U.S. Appl. No. 17/725,370, filed Apr. 20, 2022 Notice of Allowance dated Sep. 18, 2024.
U.S. Appl. No. 17/825,976, filed May 26, 2022 Non-Final Office Action dated Oct. 4, 2024.
U.S. Appl. No. 17/849,455, filed Jun. 24, 2022 Final Office Action dated Nov. 7, 2024.
U.S. Appl. No. 17/981,313, filed Nov. 4, 2022 Non-Final Office Action dated Oct. 8, 2024.
U.S. Appl. No. 18/601,980, filed Mar. 11, 2024 Non-Final Office Action dated Sep. 27, 2024.
U.S. Appl. No. 17/485,035, filed Sep. 24, 2021 Notice of Allowance dated Nov. 8, 2023.
U.S. Appl. No. 17/707,662, filed Mar. 29, 2022 Advisory Action dated Feb. 23, 2024.
U.S. Appl. No. 17/707,662, filed Mar. 29, 2022 Final Office Action dated Apr. 22, 2024.
U.S. Appl. No. 17/707,662, filed Mar. 29, 2022 Final Office Action dated Dec. 20, 2023.
U.S. Appl. No. 17/724,371, filed Apr. 19, 2022 Non-Final Office Action dated Apr. 12, 2024.
U.S. Appl. No. 17/725,370, filed Apr. 20, 2022 Final Office Action dated Feb. 15, 2024.
U.S. Appl. No. 17/825,976, filed May 26, 2022 Restriction Requirement dated Apr. 12, 2024.
PCT/US2023/025845 filed Jun. 21, 2023 International Preliminary Report on Patentability dated Dec. 18, 2024.
U.S. Appl. No. 17/687,476, filed Mar. 4, 2022 Notice of Allowance dated Mar. 5, 2025.
U.S. Appl. No. 17/724,371, filed Apr. 19, 2022 Final Office Action dated Mar. 7, 2025.
U.S. Appl. No. 17/825,976, filed May 26, 2022 Final Office Action dated Mar. 25, 2025.
U.S. Appl. No. 17/841,541, filed Jun. 15, 2022 Non-Final Office Action dated Mar. 14, 2025.
U.S. Appl. No. 17/849,455, filed Jun. 24, 2022 Advisory Action dated Dec. 17, 2024.
U.S. Appl. No. 17/849,455, filed Jun. 24, 2022 Non-Final Office Action dated Jan. 24, 2025.
U.S. Appl. No. 17/859,980, filed Jul. 7, 2022 Advisory Action dated Feb. 10, 2025.
U.S. Appl. No. 17/859,980, filed Jul. 7, 2022 Final Office Action dated Dec. 5, 2024.
U.S. Appl. No. 17/965,657, filed Oct. 13, 2022 Non-Final Office Action dated Jan. 6, 2025.
U.S. Appl. No. 17/987,717, filed Nov. 15, 2022 Non-Final Office Action dated Mar. 21, 2025.
U.S. Appl. No. 18/601,980, filed Mar. 11, 2024 Notice of Allowance dated Jan. 10, 2025.
Beigi, P. et al., "Enhancement of needle visualization and localization in ultrasound." International Journal of Computer Assisted Radiology and Surgery, vol. 16, No. 130, Sep. 2020 [Sep. 30, 2020] pp. 169-178.
PCT/US2023/018340 filed Apr. 12, 2023 International Seach Report and Written Opinion dated Jul. 20, 2023.

U.S. Appl. No. 17/725,370, filed Apr. 20, 2022 Non-Final Office Action dated Aug. 4, 2023.
U.S. Appl. No. 17/724,371, filed Apr. 19, 2022 Advisory Action dated May 14, 2025.
U.S. Appl. No. 17/724,371, filed Apr. 19, 2022 Non-Final Office Action dated Jun. 12, 2025.
U.S. Appl. No. 17/825,976, filed May 26, 2022 Advisory Action dated Jun. 9, 2025.
U.S. Appl. No. 17/825,976, filed May 26, 2022 Non-Final Office Action dated Aug. 5, 2025.
U.S. Appl. No. 17/841,541, filed Jun. 15, 2022 Final Office Action dated Jul. 23, 2025.
U.S. Appl. No. 17/849,455, filed Jun. 24, 2022 Advisory Action dated Jul. 11, 2025.
U.S. Appl. No. 17/849,455, filed Jun. 24, 2022 Final Office Action dated May 7, 2025.
U.S. Appl. No. 17/849,455, filed Jun. 24, 2022 Non-Final Office Action dated Sep. 5, 2025.
U.S. Appl. No. 17/859,980, filed Jul. 7, 2022 Non-Final Office Action dated May 29, 2025.
U.S. Appl. No. 17/965,657, filed Oct. 13, 2022 Final Office Action dated May 22, 2025.
U.S. Appl. No. 17/981,313, filed Nov. 4, 2022 Advisory Action dated Jun. 26, 2025.
U.S. Appl. No. 17/981,313, filed Nov. 4, 2022 Final Office Action dated Apr. 15, 2025.
U.S. Appl. No. 17/981,313, filed Nov. 4, 2022 Non-Final Office Action dated Jul. 22, 2025.
U.S. Appl. No. 17/987,717, filed Nov. 15, 2022 Notice of Allowance dated Jul. 15, 2025.
U.S. Appl. No. 17/724,371, filed Apr. 19, 2022 Final Office Action dated Jul. 24, 2024.
U.S. Appl. No. 17/849,455, filed Jun. 24, 2022 Non-Final Office Action dated Jul. 18, 2024.
U.S. Appl. No. 17/859,980, filed Jul. 7, 2022 Non-Final Office Action dated Jul. 1, 2024.
PCT/US2023/018680 filed Apr. 14, 2023 International Seach Report and Written Opinion dated Aug. 11, 2013.
PCT/US2023/023616 filed May 25, 2023 International Search Report and Written Opinion dated Aug. 16, 2023.
PCT/US2023/025259 filed Jun. 14, 2023 International Search Report and Written Opinion dated Sep. 25, 2023.
PCT/US2023/025845 filed Jun. 21, 2023 International Search Report and Written Opinion dated Sep. 26, 2023.
PCT/US2023/027042 filed Jul. 6, 2023 International Search Report and Written Opinion dated Oct. 10, 2023.
Schmidt G A et al Ultrasound-guided 1-22 vascular access in critical illness Intensive Care Medicine Springer Berlin Heidelberg Berlin/Heidelberg vol. 45 No. 4 Feb. 18, 2019 Feb. 18, 2019 pp. 434-446 XP036747515 ISSN 0342-4542 DOI 10.1007/500134-019-05564-7 retrieved on 2019-02-181.
U.S. Appl. No. 17/707,662, filed Mar. 29, 2022 Non-Final Office Action dated Oct. 17, 2023.
U.S. Appl. No. 17/724,371, filed Apr. 19, 2022 Final Office Action dated Oct. 29, 2025.
U.S. Appl. No. 17/859,980, filed Jul. 7, 2022 Final Office Action dated Oct. 16, 2025.
U.S. Appl. No. 17/965,657, filed Oct. 13, 2022 Notice of Allowance dated Sep. 24, 2025.

* cited by examiner

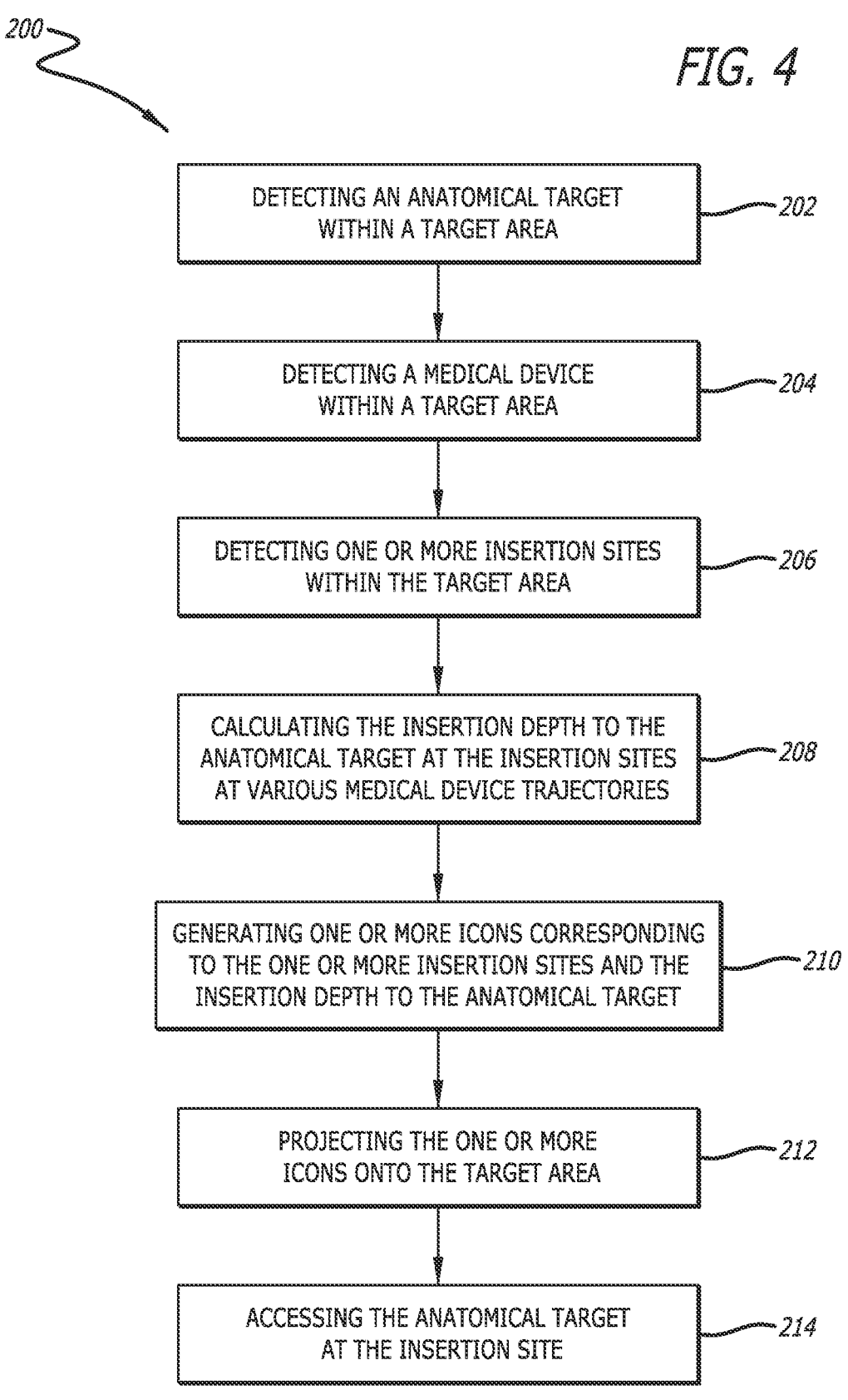

DETECTING AN ANATOMICAL TARGET
WITHIN A TARGET AREA — 202

DETECTING A MEDICAL DEVICE
WITHIN A TARGET AREA — 204

DETECTING ONE OR MORE INSERTION SITES
WITHIN THE TARGET AREA — 206

CALCULATING THE INSERTION DEPTH TO THE
ANATOMICAL TARGET AT THE INSERTION SITES
AT VARIOUS MEDICAL DEVICE TRAJECTORIES — 208

GENERATING ONE OR MORE ICONS CORRESPONDING
TO THE ONE OR MORE INSERTION SITES AND THE
INSERTION DEPTH TO THE ANATOMICAL TARGET — 210

PROJECTING THE ONE OR MORE
ICONS ONTO THE TARGET AREA — 212

ACCESSING THE ANATOMICAL TARGET
AT THE INSERTION SITE — 214

ULTRASOUND DETECTION SYSTEM

PRIORITY

This application claims the benefit of priority to U.S. Provisional Application No. 63/213,576, filed Jun. 22, 2021, which is incorporated by reference in its entirety into this application.

BACKGROUND

Readily detecting and accessing a blood vessel using an ultrasound detection system can require a user to detect and access the blood vessel in a target area but view the detection of the blood vessel on a screen in another area. Having the user focusing their attention on two separate locations can lead to confusion on where to access the blood vessel and additional time needed to confirm the proper location for blood vessel access. It would be advantageous to have an ultrasound detection system that allowed a user to detect a blood vessel, view the detection of the blood vessel, confirm the access location for the blood vessel, and access the blood vessel all within the target area. Disclosed herein is an ultrasound detection system and method of use that address the foregoing.

SUMMARY

Disclosed herein is an ultrasound imaging system configured to guide medical device insertion. The system, according to some embodiments, includes: an ultrasound probe having an ultrasound generation device configured to detect one or more anatomical targets within a target area; one or more projectors configured to project one or more icons within the target area; and a console coupled to the ultrasound probe and in communication with each of the ultrasound generation device and the one or more projectors, where the console is configured to generate the one or more icons.

In some embodiments, the ultrasound probe includes one or more sensors configured to detect and track the location and orientation of a medical device within the target area, where the one or more sensors are in communication with the console.

In some embodiments, the one or more sensors are configured to detect and track the location and orientation of the medical device using a magnetic signature of the medical device.

In some embodiments, the orientation of the medical device includes the angle of trajectory of the medical device in relation to the ultrasound probe.

In some embodiments, the console includes one or more processors, an energy source, non-transitory computer readable medium and a plurality of logic modules.

In some embodiments, the plurality of logic modules, when executed by the processor, are configured to perform operations including (i) receiving ultrasound signals from the ultrasound probe, (ii) detecting the one or more anatomical targets within the target area, (iii) detecting and tracking the location and orientation of the medical device within the target area, (iv) determining one or more insertion sites within the target area to access the one or more anatomical targets, (v) calculating the insertion depth from the one or more insertion sites to the one or more anatomical targets along an angle of trajectory of the medical device, generating one or more icons, and (vi) projecting the one or more icons on a skin surface within the target area.

In some embodiments, the one or more projectors include one or more lasers.

In some embodiments, the one or more icons include icons having a shape, a size, a color, and an orientation in relation to either the ultrasound probe or the user.

In some embodiments, the one or more icons correspond to (i) the one or more insertion sites and (ii) the calculated insertion depth from the one or more insertion sites to the one or more anatomical targets along the angle of trajectory of the medical device.

In some embodiments, the one or more insertion sites are determined at specific locations within the target area relative to the ultrasound probe.

In some embodiments, the one or more insertion sites are determined based on predefined insertion depths within the target area.

In some embodiments, the one or more insertion sites are determined using one or more pre-determined angles of trajectory of the medical device.

In some embodiments, the medical device is a needle.

In some embodiments, the one or more anatomical targets include one or more blood vessels within the target area.

Also disclosed herein is a method of detecting and accessing an anatomical target. According to some embodiments, the method includes: detecting the anatomical target within a target area; detecting a medical device within the target area; determining one or more insertion sites within the target area to access the anatomical target; calculating the insertion depth to the anatomical target at any of the insertion sites; generating one or more icons corresponding to (i) the one or more insertion sites and (ii) the insertion depth to the anatomical target; projecting the one or more icons on the target area; and accessing the anatomical target at the insertion site.

In some embodiments of the method, detecting the anatomical target within the target area includes detecting the anatomical target with an ultrasound probe having an ultrasound generation device configured to generate and detect ultrasound signals, where the ultrasound probe is in communication with a console configured to receive the ultrasound signals.

In some embodiments of the method, detecting the medical device within the target area includes one or more sensors that are in communication with the console and that are coupled to the ultrasound probe, where the one or more sensors detect the location and orientation of the medical device.

In some embodiments of the method, the one or more sensors detect a magnetic signature of the medical device, and in further embodiments, the magnetic signature of the medical device is unique.

In some embodiments of the method, the one or more sensors detect an angle of trajectory of the medical device in relation to the one or more sensors.

In some embodiments of the method, determining the one or more insertion sites within the target area includes the console determining the one or more insertion sites.

In some embodiments of the method, the console determines the one or more insertion sites at specific locations relative to the ultrasound probe.

In some embodiments of the method, the console determines the one or more insertion sites by using pre-determined angles of trajectory of the medical device to determine the one or more insertion sites.

In some embodiments of the method, the console determines the one or more insertion sites based on predefined insertion depths within the target area.

In some embodiments of the method, calculating the insertion depth to the anatomical target at any of the insertion sites includes the console calculating the insertion depth to the anatomical target along the angle of trajectory of the medical device at any of the insertion sites.

In some embodiments of the method, the console calculates the insertion depth to the anatomical target along either the detected angle of trajectory of the medical device or a pre-determined angle of trajectory of the medical device.

In some embodiments of the method, generating one or more icons corresponding to the one or more insertion sites and the insertion depth to the anatomical target includes generating a first icon having a shape and a color corresponding to the insertion site and a second icon having text corresponding to the insertion depth to the anatomical target along the angle of trajectory of the medical device.

In some embodiments of the method, generating one or more icons includes generating one or more new icons when the angle of trajectory of the medical device changes.

In some embodiments of the method, generating one or more new icons when the angle of trajectory of the medical device changes includes generating one or more new icons configured to indicate to the user when the angle of trajectory of the medical device is in line with the pre-determined angle of trajectory.

In some embodiments of the method, projecting the one or more icons on the target area includes one or more projectors projecting the one or more icons on the target area, where the one or more projectors are in communication with the console and are coupled to the ultrasound probe.

In some embodiments of the method, projecting the one or more icons on the target area includes the one or more projectors projecting the one or more icons on a skin surface of the target area.

In some embodiments of the method, the one or more projectors include one or more lasers.

In some embodiments of the method, accessing the anatomical target at the insertion site includes the medical device accessing the anatomical target.

In some embodiments of the method, accessing the anatomical target at the insertion site includes inserting the medical device into the insertion site along a pre-determined angle of trajectory or the detected angle of trajectory.

In some embodiments of the method, accessing the anatomical target includes inserting the medical device through the one or more icons to access the target blood vessel.

In some embodiments of the method, the anatomical target includes one or more blood vessels within the target area.

These and other features of the concepts provided herein will become more apparent to those of skill in the art in view of the accompanying drawings and following description, which describe particular embodiments of such concepts in greater detail.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIG. 4 illustrates a flow chart of an exemplary method of detecting and accessing an anatomical target within a target area, in accordance with some embodiments.

DESCRIPTION

Figure 1:
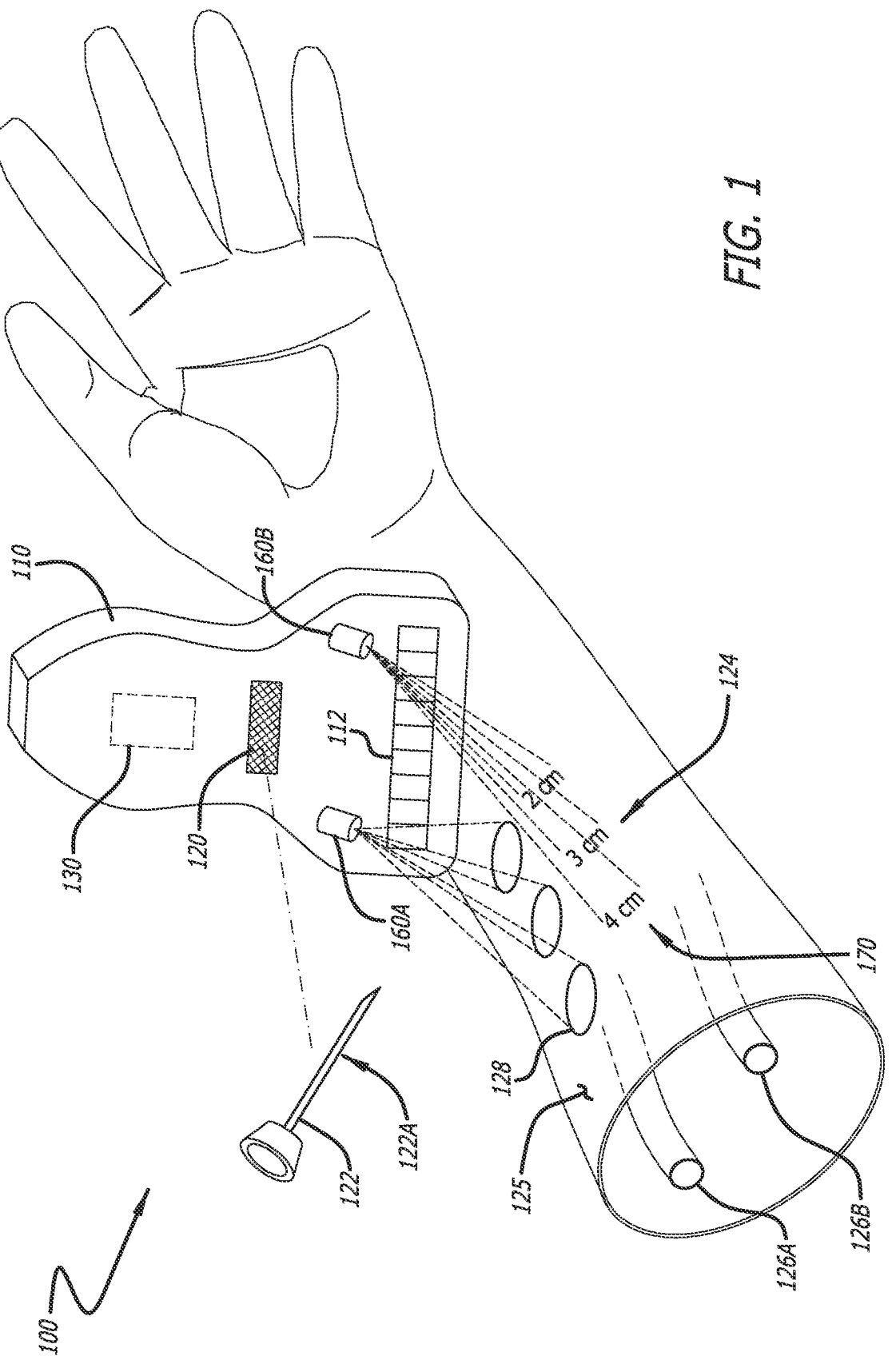
FIG. 1 illustrates a perspective view of an ultrasound detection system, in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

The term "logic" may be representative of hardware, firmware or software that is configured to perform one or more functions. As hardware, the term logic may refer to or include circuitry having data processing and/or storage functionality. Examples of such circuitry may include, but are not limited or restricted to a hardware processor (e.g., microprocessor, one or more processor cores, a digital signal processor, a programmable gate array, a microcontroller, an application specific integrated circuit "ASIC", etc.), a semiconductor memory, or combinatorial elements.

Additionally, or in the alternative, the term logic may refer to or include software such as one or more processes, one or more instances, Application Programming Interface(s) (API), subroutine(s), function(s), applet(s), servlet(s), routine(s), source code, object code, shared library/dynamic link library (dll), or even one or more instructions. This software may be stored in any type of a suitable non-transitory storage medium, or transitory storage medium (e.g., electrical, optical, acoustical or other form of propagated signals such as carrier waves, infrared signals, or digital signals). Examples of a non-transitory storage medium may include, but are not limited or restricted to a programmable circuit; non-persistent storage such as volatile memory (e.g., any type of random access memory "RAM"); or persistent storage such as non-volatile memory (e.g., read-only memory "ROM", power-backed RAM, flash memory, phase-change memory, etc.), a solid-state drive, hard disk drive, an optical disc drive, or a portable memory device. As firmware, the logic may be stored in persistent storage.

Unless defined otherwise, all technical and scientific terms used herein have the same meaning as commonly understood by those of ordinary skill in the art.

FIG. 1 illustrates a perspective view of an ultrasound imaging system 100 including an ultrasound probe 110 having one or more projectors 160A-160B thereon, in accordance with some embodiments. In some embodiments, the ultrasound imaging system 100 may be configured to guide medical device insertion. The ultrasound probe 110 may be configured to detect one or more anatomical targets within a target area 124 by contacting a skin surface within the target area 124. In some embodiments, the ultrasound probe 110 may include an ultrasound generation device 112 including an ultrasound acoustic stack or other various modalities of ultrasound generation. The ultrasound generation device 112 may be configured to direct ultrasound waves into the target area 124 and detect reflections of the ultrasound waves. In some embodiments, the target area 124 may include one or more anatomical targets 126A-126B to be accessed by a medical device 122. Although the illustrated one or more anatomical targets 126A-126B include two anatomical targets, in other embodiments, the one or more anatomical targets may include 1, 3, 4, or more anatomical targets. In the illustrated embodiment, the one or more anatomical targets 126A-126B include blood vessels and as such the anatomical targets may be referred to as blood vessels herein below. However, in other embodiments the anatomical targets may include anatomical elements other than blood vessels. In some embodiments, the medical device 122 may include a vascular access device including a catheter, peripherally inserted central catheter ("PICC"), peripheral intravenous line ("Ply"), central venous catheter ("CVC"), midline catheter, a needle, or the like. In some embodiments, the medical device 122 may include ferrous elements configured to contain a magnetic signature 122A imprinted therein or otherwise coupled with the medical device 122, the magnetic signature 122A configured to be detected and tracked in three-dimensional space by one or more sensors 120 coupled to the ultrasound probe 110. In some embodiments, the one or more sensors 120 may be configured to detect and track the location of the medical device 122 in relation to the one or more sensors 120 (or the ultrasound probe 110 as a whole) and the orientation including the angle of trajectory of the medical device 122 in relation to the one or more sensors 120 (or the ultrasound probe 110 as a whole). Examples of magnetic tracking of a needle by an ultrasound probe can be found, for example, in U.S. Pat. Nos. 9,456,766; 9,492,097; 9,554,716; 10,449,330;

10,524,691; and US 2018/0116551, each of which is incorporated by reference in its entirety into this application.

The magnetic signature 122A may include differentiating information/data regarding the medical device 122 such that a first subset of a plurality of the medical devices 122 includes a magnetic signature that is different from the magnetic signature 122A of a second subset of the plurality of the medical devices 122. In some embodiments, the differentiating information may include model information for the medical device 122, such as a module name or model number, for example. In some embodiments, the differentiating information may include dimensional information of the medical device 122, such as a length or diameter, for example. In some embodiments, the differentiating information may include manufacturing information for the medical device 122, such as a manufacturing date or lot number, for example. In some embodiments, the differentiating information may include unique information pertaining to the medical device 122, such as a serial number, for example. As such, in some embodiments, the magnetic signature 122A for any one medical device 122 may be unique with respect to (i.e., be different from) the magnetic signature for every other medical device 122.

In some embodiments, the ultrasound probe 110 may further include a console 130 in communication with the ultrasound generation device 112. The console 130 may be configured to receive detected ultrasound signals from the ultrasound generation device 112. The ultrasound probe 110 may include the one or more sensors 120 coupled to the ultrasound probe 110, the sensors 120 configured to detect the medical device 122. The ultrasound probe 110 may also include one or more projectors 160A-160B coupled to the ultrasound probe 110, the one or more projectors 160A-160B configured to depict one or more icons 170 onto a skin surface 125 the target area 124. In some embodiments, the one or more projectors 160A-160B may be (i) in communication with the console 130 and (ii) configured to project the one or more icons 170 onto the skin surface 125 of the target area 124. In some embodiments, the one or more projectors 160A-160B may include one or more lasers. In some embodiments, the ultrasound generation device 112, the one or more sensors 120 and the one or more projectors 160A-160B may be wired to the console 130 or in wireless communication with the console 130. Exemplary wireless communication modalities can include WiFi, Bluetooth, Near Field Communications (NFC), cellular Global System for Mobile Communication ("GSM"), electromagnetic (EM), radio frequency (RF), combinations thereof, or the like.

As illustrated in FIG. 1, the ultrasound probe 110 may be configured to detect one or more anatomical targets, including one or more anatomical targets 126A-126B within the target area 124. The console 130 may be configured to detect and track the medical device 122 as the medical device 122 is moved within the target area 124. The console 130 may be configured to detect the angle of trajectory (see angle of trajectory 123 of FIG. 3A) of the medical device 122 as the medical device 122 is brought into the target area 124 to access the one or more blood vessels 126A-126B. The console 130 may be configured to determine one or more insertion sites 128 and calculate the insertion depth (see insertion depth 127 of FIG. 3A) to the one or more blood vessels 126A-126B at the insertion sites 128 along the current angle of trajectory of the medical device 122. The console 130 may be configured to generate one or more icons 170 configured to identify the insertion sites 128 to the user and the insertion depth to the one or more blood vessels 126A-126B at the insertion sites 128. In some embodiments, the one or more projectors 160A-160B may be coupled to the ultrasound probe 110 or may be formed integrally with the ultrasound probe 110. Advantageously, the one or more projectors 160A-160B may be configured to depict the one or more icons 170 corresponding to the insertion site 128 and insertion depth to the one or more blood vessels 126A-126B onto the target area 124 to help guide a user during medical device insertion. Furthermore, the one or more icons 170 allow the user to focus their full attention on the target area 124 while the one or more projectors 160A-160B depict information to guide the insertion of the medical device 122.

Figure 2:
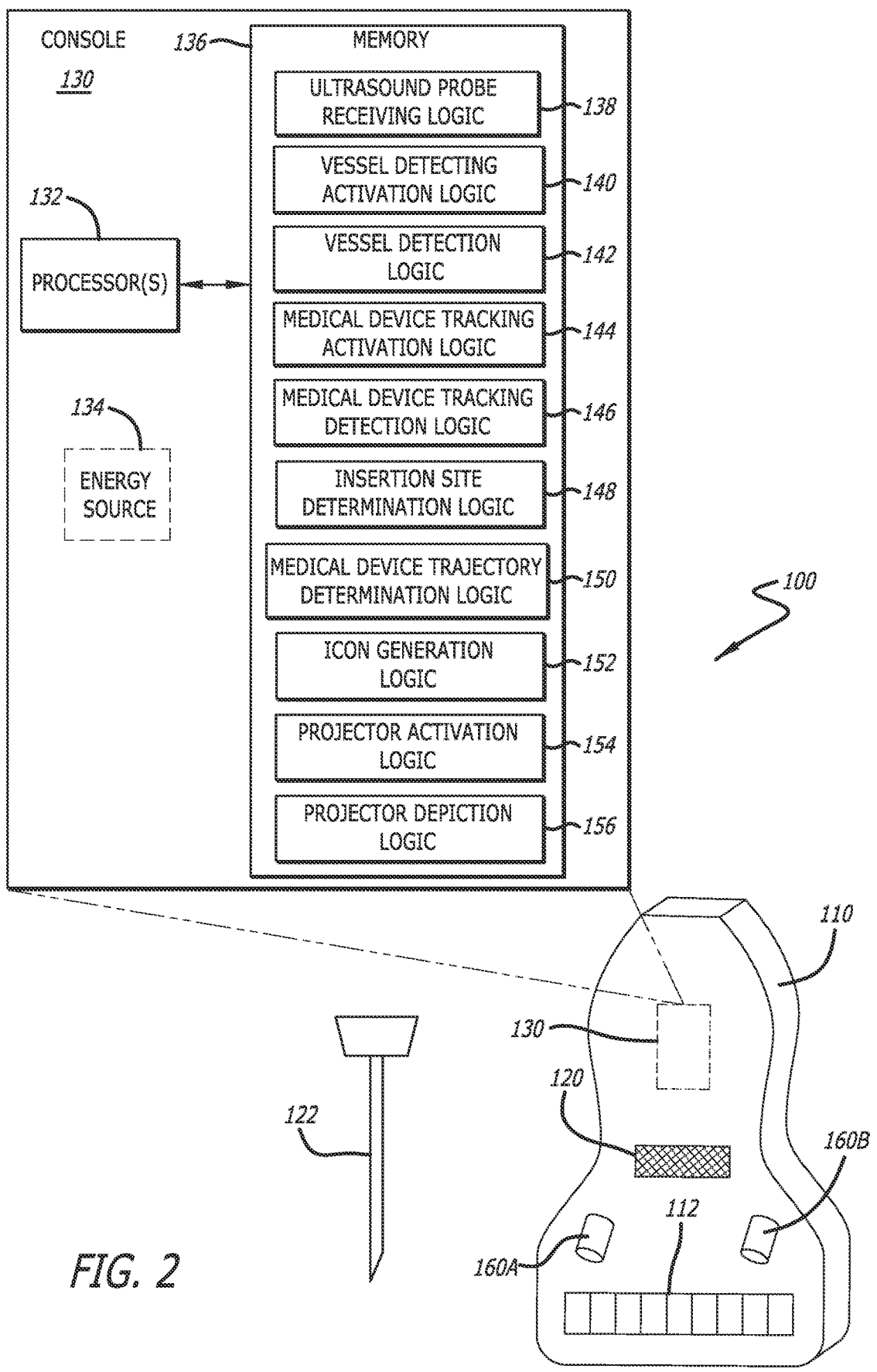
FIG. 2 illustrates a block diagram of some components of the ultrasound detection system including a console, in accordance with some embodiments.

FIG. 2 illustrates a block diagram of some components of the ultrasound imaging system 100 including the console 130 in accordance with some embodiments. In some embodiments, the console 130 includes one or more processors 132, an energy source 134, non-transitory computer readable medium ("memory") 136 and a plurality of logic modules. In some embodiments, the energy source 134 may be configured to provide power to the one or more projectors 160A-160B, the one or more sensors 120, and the ultrasound generation device 112. In some embodiments, the plurality of logic modules may include one or more of: an ultrasound probe receiving logic 138, a vessel detecting activation logic 140, a vessel detection logic 142, a medical device tracking activation logic 144, a medical device tracking detection logic 146, an insertion site determination logic 148, a medical device trajectory determination logic 150, an icon generation logic 152, a projector activation logic 154, and a projector depiction logic 156. In some embodiments, the ultrasound probe receiving logic 138 may be configured to receive the detected ultrasound signals from the ultrasound generation device 112.

In some embodiments, the vessel detecting activation logic 140 may be configured to activate detection of the one or more anatomical targets 126A-126B within the target area 124 from the detected ultrasound signals. In some embodiments, the vessel detecting activation logic 140 may be activated immediately upon the console 130 receiving detected ultrasound signals.

In some embodiments, the vessel detection logic 142 may be configured to detect the one or more anatomical targets 126A-126B including the one or more blood vessels within the target area 124 from the detected ultrasound signals. In some embodiments, the vessel detection logic 142 may be configured to detect the orientation of the ultrasound probe 110 in in relation to the one or more blood vessels 126A-126B within the target area 124.

In some embodiments, the medical device tracking activation logic 144 may be configured to activate the one or more sensors 120 to track the medical device 122 moving through the target area 124. In some embodiments, the medical device tracking detection logic 146 may be configured to detect and track the medical device 122, as the medical device 122 moves through the target area 124 using the one or more sensors 120. In some embodiments, the medical device tracking detection logic 146 may detect the magnetic signature 122A of the medical device 122. In some embodiments, the medical device tracking detection logic 146 may be configured to detect and track the location of the medical device 122 and the orientation of the medical device 122 including the angle of trajectory of the medical device 122 in relation to the one or more sensors 120 or the ultrasound probe 110 as whole.

In some embodiments, the insertion site determination logic 148 may be configured to determine one or more insertion sites 128 within the target area 124 for accessing the one or more blood vessels 126A-126B. The insertion sites 128 may be the one or more locations on the skin surface 125 of the target area 124 wherein the medical device 122 may access the one or more blood vessels 126A-126B along an angle of trajectory. In some embodiments, the one or more insertion sites 128 may be determined using pre-determined angles of trajectory for the medical device 122. For example, pre-determined angles of trajectory in relation to the blood vessels 126A-126B of 35° or 45° of the medical device 122 accessing the one or more blood vessels 126A-126B may be used to determine the location of the insertion sites 128 within the target area 124. In some embodiments, the insertion site determination logic 148 may be configured to determine the one or more insertion sites 128 relative to the ultrasound probe 110. In some embodiments, the insertion site determination logic 148 may be configured to determine the one or more insertion sites 128 at pre-defined insertion depths. In some embodiments, the insertion site determination logic 148 may be configured to determine the one or more insertion sites 128 within the target area 124 for accessing the one or more blood vessels 126A-126B using information about the medical device 122 (e.g., the make and model of the medical device, the length of the medical device, or the like) to determine the one or more insertion sites 128.

In some embodiments, the medical device trajectory determination logic 150 may be configured to determine the angle of trajectory of the medical device 122 in relation to a target one of the blood vessels 126A-126B (i.e. the target blood vessel 126A), and calculate the insertion depth to which the medical device 122 needs be inserted into the target area 124 to access the target blood vessel 126A along the detected angle of trajectory of the medical device 122 at the one or more insertion sites 128. As the current angle of trajectory of the medical device 122 changes, the medical device trajectory determination logic 150 may be configured to determine a new insertion depth to which the medical device 122 needs to be inserted into the target area 124 to access the target blood vessel 126A at the one or more insertion sites 128. In some embodiments, as the detected angle of trajectory changes, the insertion site determination logic 150 may determine one or more new insertion sites 128 to access the target blood vessel 126A. The medical device trajectory determination logic 150 may then determine the insertion the medical device 122 needs to be insertion into the target area 124 to access the target blood vessel 126A along the detected angle of trajectory of the medical device 122 at the one or more new insertion sites 128. In some embodiments, the medical device trajectory determination logic 150 may calculate the insertion depth the medical device 122 needs to be inserted into the target area 124 using user pre-determined angles of trajectory.

In some embodiments, the icon generation logic 152 may be configured to generate the one or more icons 170 configured to be depicted onto a skin surface 125 within the target area 124. In some embodiments, the one or more icons 170 may include (i) one or more insertion site location icons 170 configured to indicate the one or more insertion sites 128 and (ii) one or more vessel insertion icons 170 configured to indicate the calculated insertion depth to the target blood vessel 126A. In some embodiments, the one or more icons 170 may include various shapes (e.g., circle, square, rectangle, triangle, or the like), various sizes, various colors, various orientations, and various text. In some embodiments, the one or more icons 170 may be configured to flash, to flicker or scroll through the target area 124. In some embodiments, the various colors may correspond to type of target blood vessel 126A, the size and insertion depth of the target blood vessel 126A or the like. In some embodiments, the various text may correspond to the insertion depth in unit measurement (e.g., centimeters, inches, or the like) or may correspond to the pre-determined angle of trajectory (e.g., 120°, 65° or the like) of the medical device 122. In some embodiments, the orientation of the one or more icons 170 may be changed. For example, the one or more icons 170 may be depicted on the target area in a transverse view, a longitudinal view, or a combination thereof. In some embodiments, the orientation of the one or more icons 170 may be changed in relation to the ultrasound probe 110. In some embodiments, the user may determine the shape, size, color and orientation of the one or more icons 170.

In some embodiments, the projector activation logic 154 may be configured to activate the one or more projectors 160A-160B. In some embodiments, the projector activation logic 154 may activate the one or more projectors 160A-160B upon starting up the system 100. In some embodiments, the projector depiction logic 156 may be configured to project the one or more icons 170 onto the skin surface 125 in the target area 124. In some embodiments, user pre-determined angles of trajectory are used to (i) determine the one or more insertion sites 128 and (ii) calculate the insertion depth to the target blood vessel 126A. In some embodiments, the projector depiction logic 156 may be configured to change the shape, color, or size of the one or more icons 170 when the medical device 122 is angled at one or more predetermined angles of trajectory 123. In some embodiments, once the medical device 122 is confirmed to be inserted into the target blood vessel 126A, the projector depiction logic 156 may be configured to cease projecting the one or more icons 170 on the target area 124. In some embodiments, the projector depiction logic 156 may be configured to project the one or more icons 170 at different orientations in relation to the ultrasound probe 110 or the user.

Figures 3A, 3B:
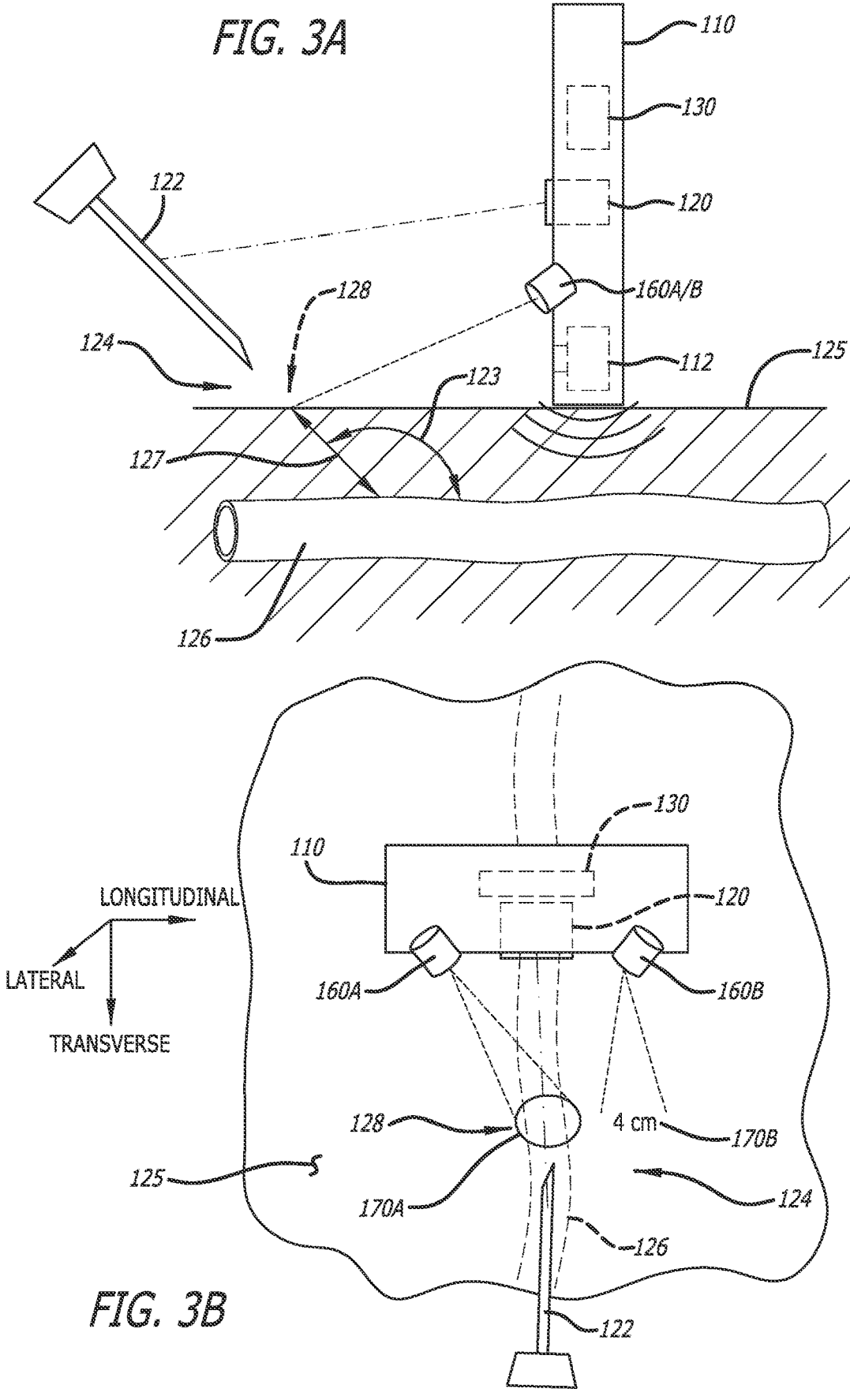
FIG. 3A illustrates a cross sectional side view of the ultrasound detection system detecting an anatomical target within the target area and calculating the insertion depth to the anatomical target along an angle of trajectory of a medical device, in accordance with some embodiments.
FIG. 3B illustrates a plan view of the ultrasound detection system detecting an anatomical target within the target area and projecting one or more icons on the target area, in accordance with some embodiments.

FIG. 3A illustrates a cross sectional view of the system 100 detecting and calculating the insertion depth 127 to the anatomical target 126A-126B, in accordance with some embodiments. The ultrasound probe 110 is as described above. The ultrasound probe 110 detects the one or more blood vessels 126A-126B within the target area 124. The console 130 may be configured to track the medical device 122 within the target area 124 using the one or more sensors 120. The console 130 may be configured to (i) determine the one or more insertion sites 128 within the target area 124, (ii) generate the one or more icons 170 corresponding to the one or more insertion sites 128, and (iii) depict the one or more icons 170 on the target area 124 via the one or more projectors 160A-160B. As the medical device 122 is moved within the target area 124, the one or more sensors 120 may be configured to (i) determine the angle of trajectory 123 of the medical device 122 in relation to the one or more sensors 120 coupled to the ultrasound probe 110 and (ii) transmit the detected angle of trajectory 123 of the medical device 122 to the console 130. The console 130 may use the detected angle of trajectory 123 of the medical device 122 in relation to the target blood vessel 126A to determine the insertion depth 127 to which the medical device 122 needs to be inserted into the target area 124 at the insertion site 128 to access the target blood vessel 126A along the detected angle of trajectory 123 of the medical device 122. For example, an angle of trajectory 123 (e.g., the illustrated angle 123 of about 135 degrees in FIG. 3A for example) of the medical device 122 in relation to the target blood vessel 126A leads to a greater insertion depth 127 to which the medical device 122 must travel through the target area 124 to access the target blood vessel 126A. The console 130 may be configured to update the one or more icons 170 depicted by the one or more projectors 160A-160B as the detected angle of trajectory 123 of the medical device 122 within the target area 124 changes.

FIG. 3B illustrates a plan view of the system 100 of FIG. 3A detecting the medical device 122 within the target area 124 and the one or more projectors 160A-160B depicting the one or more icons 170 on the skin surface 125 within the target area 124, in accordance with some embodiments. The ultrasound probe 110 is configured to detect the target blood vessel 126A within the target area 124 as described above. The medical device 122 is detected by the one or more sensors 120 coupled to the ultrasound probe 110 as the ultrasound probe 110 is within the target area 124 as described above. As illustrated in FIG. 3B, the console 130 is configured to generate the icon 170A corresponding to the one or more insertion sites 128 and the icon 170B corresponding to the insertion depth 127 of the target vessel 126A along the angle of trajectory 123 of the medical device 122 at that specific insertion site 128. The projectors 160A-160B may be configured to depict the icons 170A-170B within the target area 124. The icons 170A-170B may be configured in the target area 124 to be adjacent and longitudinally in line with each other to enable the user to quickly identify the insertion site 128 and the insertion depth 127 to the target blood vessel 126A.

Figures 3C, 3D:
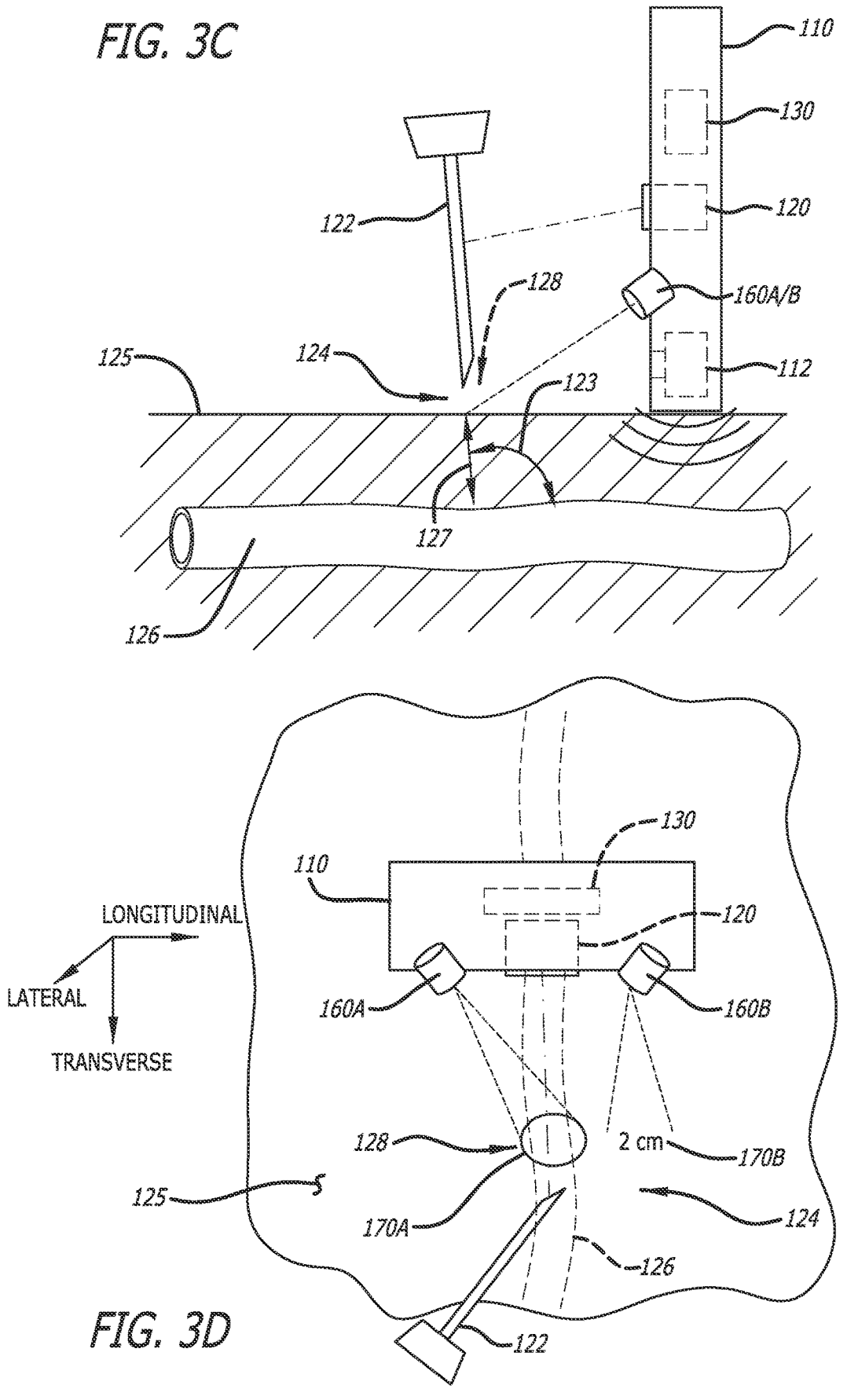
FIG. 3C illustrates a cross sectional side view of the ultrasound detection system detecting an anatomical target within the target area and calculating the insertion depth to the anatomical target along an angle of trajectory of a medical device, in accordance with some embodiments.
FIG. 3D illustrates a plan view of the ultrasound detection system detecting an anatomical target within the target area and projecting one or more icons on the target area, in accordance with some embodiments.

FIG. 3C illustrates a cross sectional side view of the system 100 detecting and calculating the insertion depth 127 to the anatomical target 126, in accordance with some embodiments. As illustrated in FIG. 3C, the angle of trajectory 123 of the medical device 122 (e.g., the illustrated angle 123 of about 95 degrees in FIG. 3C for example) is more acute than the angle of trajectory 123 of the medical device 122 illustrated in FIG. 3A. Thus, the calculated insertion depth 127 that the medical device 122 needs to travels within the target area 124 in order to access the target blood vessel 126A in FIG. 3C is less than the calculated insertion depth 127 that the medical device 122 needed to travel in FIG. 3A.

FIG. 3D illustrates a plan view of the system 100 of FIG. 3C detecting the medical device 122 within the target area 124 and the one or more projectors 160A-160B depicting the icons 170A-170B within the target area 124, in accordance with some embodiments. The icon 170B may be configured to indicate the calculated insertion depth 127 in FIG. 3C. Furthermore, the projectors 160A-160B may depict the icon 170B oriented in the transverse direction, giving the user multiple viewing options of the icons 170A-170B.

FIG. 4 illustrates a flow chart of an exemplary method 200 of detecting and accessing an anatomical target such as the blood vessel 126A, in accordance with some embodiments. In some embodiments, the method 200 includes detecting the blood vessel 126A within the target area 124 (block 202). In some embodiments, detecting the blood vessel 126A within the target area 124 includes using the ultrasound probe 110 having the ultrasound generation device 112 to detect the blood vessel 126A. In some embodiments, detecting the blood vessel 126A within the target area 124 includes contacting the skin surface 125 of the target area 124 with the ultrasound probe 110.

The method 200 further includes detecting the medical device 122 within the target area 124 (block 204). In some embodiments, detecting the medical device 122 within the target area 124 includes the one or more sensors 120 detecting the medical device 122 within the target area 124.

In some embodiments, the one or more sensors 120 may detect the magnetic signature 122A of the medical device 122. In some embodiments, the one or more sensors 120 may detect and communicate to the console 130 the location of the medical device 122 within the target area 124 and the orientation of the medical device 122 in relation to the one or more sensors 120 coupled to the ultrasound probe 110.

The method 200 further includes determining one or more insertions sites 128 within the target area 124 to access the blood vessel 126A (block 206). In some embodiments, determining the one or more insertion sites 128 includes the console 130 determining the one or more insertion sites 128. In some embodiments, the one or more insertion sites 128 may be determined by using pre-determined angles of trajectory to determine the one or more insertion sites 128 within the target area 124. In some embodiments, the one or more insertion sites 128 may be determined predefined insertion depths. In some embodiments, the one or more insertion sites 128 may be determined at specific locations relative to the ultrasound probe 110.

The method 200 further includes calculating the insertion depth 127 to the blood vessel 126A at the one or more insertion sites 128 (block 208). In some embodiments, the console 130 is configured to calculate the insertion depth 127 to the blood vessel 126A at the one or more insertion sites 128. In some embodiments, the console 130 calculates the insertion depth 127 to the blood vessel 126A using the detected angle of trajectory 123 of the medical device 122 to calculate the insertion depth 127 at the one or more insertion sites 128. In some embodiments, the console 130 uses pre-determined angles of trajectory of the medical device 122 to calculate the insertion depth 127 to the blood vessel 126A at the one or more insertion sites 128. In some embodiments, the console 130 may use pre-determined insertion depths to define the one or more insertion sites. In other words, the insertion sites 128 may be defined to correspond with defined insertion depths 127, such as 2 cm, 3 cm, or 4 cm, for example.

The method 200 further includes generating (i) one or more icons 170, the one or more icons 170 corresponding to the one or more insertion sites 128 and (ii) the insertion depth 127 to the target blood vessel 126A at the one or more insertion sites 128 (block 210). In some embodiments, the console 130 may be configured to generate the one or more icons 170. In some embodiments, the one or more icons 170 may include a variety of shapes, colors, text, sizes, or the like. In some embodiments, a first icon 170 having a shape, a size and a color may correspond to the insertion site 128 and a second icon 170, having text, that may correspond to the insertion depth 127 to the blood vessel 126A at the insertion site 128 along the detected angle of trajectory 123 of the medical device 122. In an embodiment, a single icon 170 having a shape, a size, a color and text within the shape may correspond to both the insertion site 128 and the insertion depth 127 to the blood vessel 126A at the insertion site 128 along the detected angle of trajectory 123 of the medical device 122. In some embodiments, generating one or more icons 170 includes generating (i) one or more new icons 170 corresponding to the one or more insertion sites 128 and (ii) the insertion depth 127 to the anatomical target 126 at the one or more insertion sites 128 when the angle of trajectory 123 of the medical device 122 changes. In some embodiments, generating one or more new icons 170 includes generating one or more new icons 170 configured to indicate to the user that the angle of trajectory 123 of the medical device 122 is in line with one of the pre-determined angles of trajectory 123. In some embodiments, generating the one or more new icons 170 includes changing one or more of the size, the shape, or the color of the new icons 170 to indicate to the user that the angle of trajectory 123 of the medical device 122 is in line with one of the pre-determined angles of trajectory 123.

The method 200 further includes projecting the one or more icons 170 on the target area 124 (block 212). In some embodiments, projecting the one or more icons 170 on the target area 124 includes the one or more projectors 160A-160B projecting the one or more icons 170 on the skin surface 125 within the target area 124. In some embodiments, projecting the one or more icons 170 on the target area 124 includes the one or more projectors 160A-160B projecting the one or more icons 170 on the target area 124 in different orientations in relation to the ultrasound probe 110 or the user.

The method 200 further includes accessing the blood vessel 126A at the insertion site 128 (block 214). In some embodiments, accessing the blood vessel 126A at the insertion site 128 includes inserting the medical device 122 into the insertion site 128 along the detected angle of trajectory 123 to access the blood vessel 126A. In some embodiments, inserting the medical device 122 into the insertion site 128 includes inserting the medical device 122 through the icon 170 projected onto the target area 124 corresponding to the insertion site 128. In some embodiments, inserting the medical device 122 into the insertion site 128 includes inserting the medical device the calculated insertion depth 127 depicted by the icon 170 on the target area 124.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. An ultrasound imaging system configured to guide medical device insertion, comprising:
   an ultrasound probe comprising:
   an ultrasound generation device configured to detect one or more anatomical targets within a target area;
   one or more projectors configured to project one or more icons onto a skin surface within the target area, wherein the one or more icons include:
   an insertion site for a medical device; and
   a depth extending from the insertion site to the one or more anatomical targets; and
   a console coupled to the ultrasound probe and in communication with each of the ultrasound generation device and the one or more projectors, the console configured to generate the one or more icons.

2. The ultrasound imaging system according to claim 1, wherein the ultrasound probe includes one or more sensors configured to detect and track a location and an orientation of the medical device within the target area, the one or more sensors in communication with the console.

3. The ultrasound imaging system according to claim 2, wherein the one or more sensors are configured to detect and track the location and orientation of the medical device using a magnetic signature of the medical device.

4. The ultrasound imaging system according to claim 3, wherein the orientation of the medical device includes an angle of trajectory of the medical device in relation to the ultrasound probe.

5. The ultrasound imaging system according to claim 1, wherein the console includes:

one or more processors;

an energy source;

a non-transitory computer readable medium; and a plurality of logic modules.

6. The ultrasound imaging system according to claim 5, wherein the plurality of logic modules, when executed by the one or more processors, are configured to perform operations including:

receiving ultrasound signals from the ultrasound probe;

detecting the one or more anatomical targets within the target area;

detecting and tracking a location and an orientation of the medical device within the target area;

determining an insertion site within the target area to access the one or more anatomical targets;

calculating an insertion depth extending from the insertion site to the one or more anatomical targets along an angle of trajectory of the medical device;

generating the one or more icons; and projecting the one or more icons onto the skin surface within the target area.

7. The ultrasound imaging system according to claim 6, wherein the insertion site is determined at a specific location within the target area relative to the ultrasound probe.

8. The ultrasound imaging system according to claim 6, wherein the insertion site is determined based on a pre-defined insertion depth within the target area.

9. The ultrasound imaging system according to claim 6, wherein the insertion site is determined based on one or more pre-determined angles of trajectory of the medical device.

10. The ultrasound imaging system according to claim 1, wherein the one or more projectors include one or more lasers.

11. The ultrasound imaging system according to claim 1, wherein the one or more icons include icons having a shape, a size, a color and an orientation in relation to either the ultrasound probe or a user.

12. The ultrasound imaging system according to claim 1, wherein the one or more icons correspond to the insertion site and a calculated insertion depth from the insertion site to the one or more anatomical targets along an angle of trajectory of the medical device.

13. The ultrasound imaging system according to claim 1, wherein the medical device is a needle.

14. The ultrasound imaging system according to claim 1, wherein the one or more anatomical targets include one or more blood vessels within the target area.

15. A method of detecting and accessing an anatomical target, comprising:

detecting the anatomical target within a target area;

detecting a medical device within the target area;

determining an insertion site within the target area to access the anatomical target;

calculating an insertion depth to the anatomical target of the insertion site;

generating one or more icons corresponding to the insertion site, the one or more icons including the insertion depth to the anatomical target;

projecting the one or more icons on the target area; and accessing the anatomical target at the insertion site.

16. The method according to claim 15, wherein detecting the anatomical target within the target area includes detecting the anatomical target with an ultrasound probe having an ultrasound generation device configured to generate and detect ultrasound signals, the ultrasound probe in communication with a console configured to receive the ultrasound signals.

17. The method according to claim 16, wherein detecting the medical device within the target area includes one or more sensors in communication with the console and coupled to the ultrasound probe, the one or more sensors detecting a location and an orientation of the medical device with respect to the ultrasound probe.

18. The method according to claim 17, wherein the one or more sensors detect a unique magnetic signature of the medical device.

19. The method according to claim 17, wherein the one or more sensors detect an angle of trajectory of the medical device in relation to the ultrasound probe.

20. The method according to claim 15, wherein determining the insertion site within the target area includes a console determining the insertion site.

\* \* \* \* \*